United States Patent [19]

Holtkamp, Sr.

[11] Patent Number: Plant 6,985

[45] Date of Patent: Aug. 15, 1989

[54] AFRICAN VIOLET PLANT NAMED JENNIE

[76] Inventor: Reinhold Holtkamp, Sr., Werther Strasse 112, D4294 Isselburg, Fed. Rep. of Germany

[21] Appl. No.: 251,249

[22] Filed: Sep. 30, 1988

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African Violet named Jennie characterized by its relatively small, single, violet-shaped white flowers with some flowers having irregular light violet patches; strong, upright flower stems that curve slightly toward the center to form a compact bouquet above the leaves; bright green round to heart-shaped leaves, profuse flowering, vigorous growth habit, flowering 10–11 weeks after potting, and its long lasting and non-dropping flowers.

1 Drawing Sheet

The present invention comprises a new and distinct cultivar of African Violet plant, botanically known as *Saintpaulia ionantha,* and hereinafter referred to by the cultivar name Jennie.

The new cultivar was referred to during the breeding and selection process by the designation J II/I and is a product of a planned breeding program. The new cultivar was originated from a cross made by me in the controlled breeding program in Haffen, Federal Republic of Germany. The female, or seed parent was a cultivar designated H 73/3. The male, or pollen parent was a cultivar designated H 44/z.

Jennie was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Jennie has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Jennie, which in combination distinguish this African Violet as a new and distinct cultivar:

(1) Strong, upright flower stems curving slightly toward the center.
(2) Relatively small, single violet-shaped white flowers with some petals having irregular patches of light violet.
(3) Profuse flowering.
(4) Each plant carries 7–8 and more upright flower stems each of which carries 8–10 and more flowers.
(5) Long lasting, non-dropping flowers.
(6) Vigorous grower.
(7) Plant saleable 10 to 11 weeks after potting.
(8) Seed capsules push slightly through.

(9) Bright green, leather-like leaves.
(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural sunlight conditions 1 p.m. in Nashville, Tenn.

Botanical Classification: *Saintpaulia ionantha,* Ramat., c.v. Jennie.

Parentage:

*Male parent.*—H 44/z.

*Female parent.*—H 73/3.

Propagation: The new cultivar holds its distinguishing characteristics through successive propagations by leaf cuttings.

Plant: From 9 cm to 11 cm tall when grown in pots, and approximately 24–26 cm in diameter when fully grown.

*Leaves.*—General form: Round to heart-shaped. Diameter: 55–65 mm wide and 60–70 mm long. Texture: Leather-like. Aspect: Slightly hairy, slightly shiny, slightly serrated. Veins: Upperside: well visible; underside: well pronounced, light green, shiny. Color (upperside): Yellow-Green Group 146A. Color (underside): Greyed-Green Group 194 D. Petiole: Strong upright, light green, hairy.

*Flowers*—Buds: Bell-shaped 7–9 mm just before opening. Sepals: Five (5). Color: Green with brownish tough. Calyx: Shape: Funnel-shaped. Aspect: Spear-shaped, hairy. Peduncle: Character: Strong upright, hairy. Color: Green with brownish touch. Individual flowers: Size: 35–40 mm. Shape: Single violet-shaped (3 large and 2 small petals). Color (upperside): White with patches being Violet Group 88 C. Under cooler temperatures and more intensive lighting, the color of the patches tend to intensify. Color (underside): White with patches being Violet- Blue Group 91 between B and C. Borne: Each flower stem carries 8–10 and more flowers on strong, upright peduncles that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsule pushes slightly through. Filaments: Yellowish green, 4–5 mm long. Pollen Color: Yellow Group 7 A. Styles: 6–7 mm long, white, on petals with patches purplish blue, base of ovary light green and hairy.

*Roots.*—Normally developed, white when young, turning slightly brownish when older.

Disease resistance: Good.

General observations: Jennie is a very attractive, vigorous grower with white sparkling flowers and irregular light violet patches on some flowers. A tight bouquet of single violet-shaped, relatively small flowers free standing above the leaves develops after approximately 10–11 weeks. Each of the 7–8 and more strong flower stems carries 8–10 and more flowers. Occasionally an additional petal may develop. The flowers are long-lasting and non-dropping and the seed capsules push slightly through. Bright green, round to heart-shaped leaves give the plant a fresh look.

I claim:

1. A new and distinct cultivar of African Violet named Jennie, as described and illustrated, and particularly characterized by its relatively small, single, violet-shaped white flowers with some flowers having irregular light violet patches; strong, upright flower stems that curve slightly toward the center to form a compact bouquet above the leaves; bright green round to heart-shaped leaves, profuse flowering, vigorous growth habit, flowering 10–11 weeks after potting, and its long lasting and non-dropping flowers.

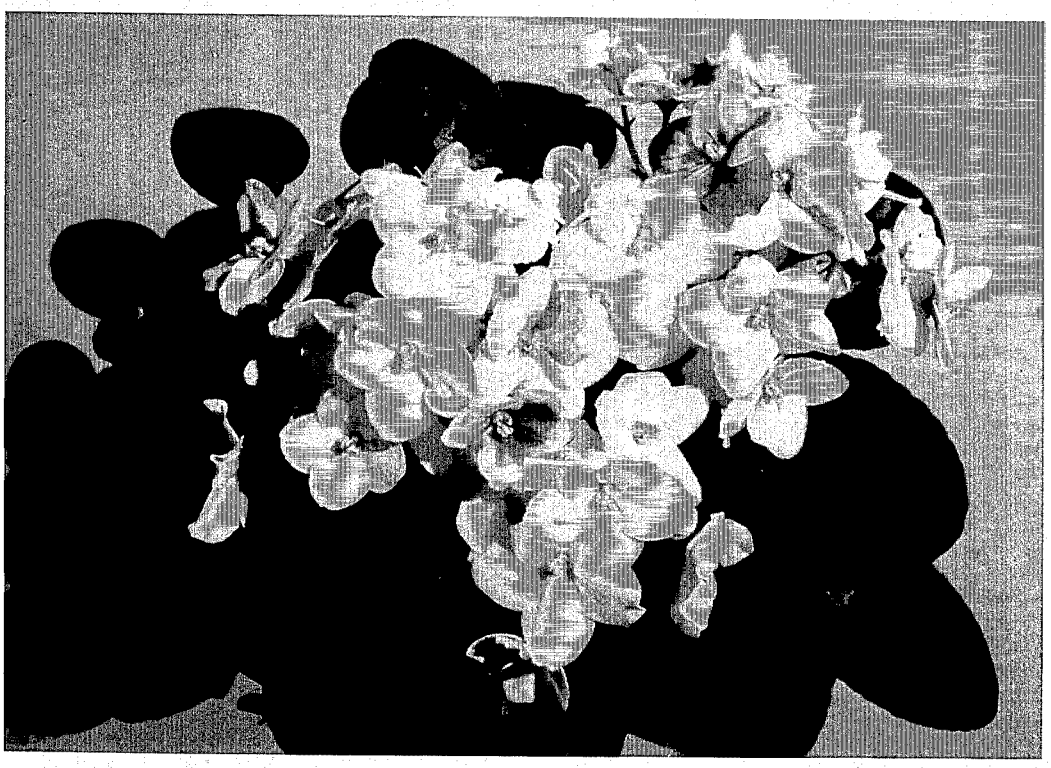

* * * * *